(12) United States Patent
Mehta et al.

(10) Patent No.: US 8,334,415 B2
(45) Date of Patent: Dec. 18, 2012

(54) PROCESS AND APPARATUS FOR REDUCING HEAVY BYPRODUCT FORMATION DURING DISTILLATION

(75) Inventors: Anil J. Mehta, Lake Jackson, TX (US); Danil Tirtowidjojo, Lake Jackson, TX (US); Jose Javier Longoria, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 522 days.

(21) Appl. No.: 12/595,468

(22) PCT Filed: Apr. 11, 2008

(86) PCT No.: PCT/US2008/059969
§ 371 (c)(1),
(2), (4) Date: Oct. 9, 2009

(87) PCT Pub. No.: WO2008/128005
PCT Pub. Date: Oct. 23, 2008

(65) Prior Publication Data
US 2010/0137621 A1    Jun. 3, 2010

Related U.S. Application Data

(60) Provisional application No. 60/923,106, filed on Apr. 12, 2007.

(51) Int. Cl.
*C07C 31/34* (2006.01)
*C07D 301/02* (2006.01)

(52) U.S. Cl. ........................................ 568/844; 549/518
(58) Field of Classification Search ............... 549/518; 568/844
See application file for complete search history.

(56) References Cited

U.S. PATENT DOCUMENTS

| 2,144,612 A | * | 1/1939 | Heindel et al. ............... 568/844 |
| 4,634,784 A | | 1/1987 | Nagato et al. |
| 2004/0045804 A1 | | 3/2004 | Bohner et al. |

FOREIGN PATENT DOCUMENTS

| CN | 101007751 A | 1/2007 |
| DE | 3520019 A1 | 4/1984 |
| EP | 0162556 A1 | 4/1985 |
| EP | 1752435 A1 | 2/2007 |
| EP | 1762556 A1 | 3/2007 |
| WO | 0240434 A1 | 5/2002 |
| WO | 2005021476 | 3/2005 |
| WO | 2005054167 A1 | 6/2005 |
| WO | 2006020234 A1 | 2/2006 |
| WO | 2008128005 A1 | 10/2008 |

OTHER PUBLICATIONS

Perry's Chemical Engineers' Handbook, 7th Edition p. 13-4.

* cited by examiner

*Primary Examiner* — Taylor Victor Oh

(57) ABSTRACT

A process and apparatus for recovering dichlorohydrins from a mixture comprising dichlorohydrins, water, one or more compounds selected from esters of dichlorohydrins, monochlorohydrins and/or esters thereof, and multihydroxylated-aliphatic hydrocarbon compounds and/or esters thereof, and optionally one or more substances comprising chlorinating agents, catalysts and/or esters of catalysts while minimizing formation of heavies is disclosed.

16 Claims, No Drawings

PROCESS AND APPARATUS FOR REDUCING HEAVY BYPRODUCT FORMATION DURING DISTILLATION

CROSS REFERENCE TO RELATED APPLICATIONS

This is a §371 application of PCT International Patent Application Number PCT/US2008/059969 filed Apr. 11, 2008, and claims priority from provisional application Ser. No. 60/923,106 filed Apr. 12, 2007, each of which is incorporated herein by reference in its entirety.

BACKGROUND OF THE INVENTION

The present invention relates to processes and apparatus for recovering, such as by distillation, dichlorohydrins from a mixture comprising the same such as the effluent generated by a process for converting multihydroxylated-aliphatic hydrocarbon compound(s) and/or ester(s) thereof to chlorohydrins.

Distillation is a well-known process for separating the components of a mixture according to their relative volatility. A liquid mixture is heated to a temperature sufficient to vaporize at least the component(s) to be separated, the vaporized component(s) is/are condensed at a location apart from (usually above) the liquid mixture, and the condensed component(s) are removed from the distillation process.

Distillation may be used to recover dichlorohydrins from a reaction mixture containing the same. Dichlorohydrins are useful in preparing epoxides such as epichlorohydrins. Epichlorohydrin is a widely used precursor to epoxy resins. Epichlorohydrin is a monomer which is commonly used for the alkylation of para-bisphenol A. The resultant diepoxide, either as a free monomer or oligomeric diepoxide, may be advanced to high molecular weight resins which are used for example in electrical laminates, can coatings, automotive topcoats and clearcoats.

Glycerin is considered to be a low-cost, renewable feedstock that is a co-product of the biodiesel process for making fuel. It is known that other renewable feedstocks such as fructose, glucose and sorbitol can be hydrogenolized to produce mixtures of vicinal diols and triols, such as glycerin, ethylene glycol, 1,2-propylene glycol, 1,3-propylene glycol and the like. With abundant and low cost glycerin or mixed glycols, economically attractive processes for recovering dichlorohydrins from effluents produced by the above processes are desired.

A process is known for the conversion of glycerol (also referred to herein as "glycerin") to mixtures of dichloropropanols, compounds I and II, as shown in Scheme 1 below. The reaction is carried out in the presence of anhydrous HCl and an acetic acid (HOAc) catalyst with water removal. Compounds I and II can then be converted to epichlorohydrin via treatment with caustic or lime.

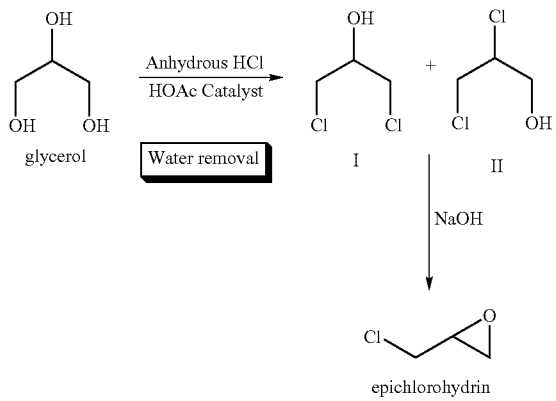

Various processes using the above chemistry in Scheme 1 have been reported in the prior art. For example, epichlorohydrin can be prepared by reacting a dichloropropanol such as 2,3-dichloro-1-propanol or 1,3-dichloro-2-propanol with base. Dichloropropanol, in turn, can be prepared at atmospheric pressure from glycerol, anhydrous hydrochloric acid, and an acid catalyst. A large excess of hydrogen chloride (HCl) was recommended to promote the azeotropic removal of water that is formed during the course of the reaction.

WO 2006/020234 A1 describes a process for conversion of a glycerol or an ester or a mixture thereof to a chlorohydrin, comprising the step of contacting a multihydroxylated-aliphatic hydrocarbon compound, an ester of a multihydroxylated-aliphatic hydrocarbon, or a mixture thereof with a source of a superatmospheric partial pressure of hydrogen chloride to produce chlorohydrins, esters of chlorohydrins, or mixtures thereof in the presence of an organic acid catalyst. This process is also referred to herein as a "dry process". Azeotropic removal of water in a dry process via a large excess of hydrogen chloride is not required to obtain high chlorohydrins yield. Separation of the product stream from the reaction mixture may be carried out with a suitable separation vessel such as one or more distillation columns among others. WO 2006/020234 A1 does not describe a specific distillation method and a method to minimize formation of heavy byproducts.

WO 2005/021476 A1 describes a process using atmospheric partial pressure of hydrogen chloride, acetic acid as the catalyst, and a cascade of loops, preferably three loops, each loop consisting of a reactor and a distillation column in which water of reaction, residual hydrogen chloride and dichloropropanol are removed from the reaction effluent. This process for distillation, requiring a cascade of reactor/distillation loops, is very expensive since the process requires several reactors/columns in the process. Furthermore, valuable acetic acid is lost with the distillate, needing to add more acetic acid to make up for the catalyst loss in distillation.

WO 2005/021476 A1 further describes that for the distillation under reduced pressure to separate the water of reaction any device for distillation can be used, such as various types of evaporators or distillation systems with various internals such as trays, packing and the like. WO 2005/021476 A1 does not distinguish between the various types of internals that can be used in the distillation regarding or the advantages of one type of internals versus another type of internals, i.e., all of the column internals are treated alike.

WO 2005/054167 A1, on page 16, describes recovery of dichloropropanol from glycerol hydrochlorination reaction effluent by distillation or evaporation. WO 2005/054167 A1 describes distillation conditions such as temperature and pressure or vacuum.

EP 1 752 435 A1 discloses another process for producing a chlorohydrin by reacting a multihydroxylated aliphatic hydrocarbon and/or an ester thereof and aqueous hydrogen chloride to produce chlorohydrins, esters of chlorohydrins, or mixtures thereof under atmospheric condition in which a purge from the reactor bottom is fed to a stripper. In the stripper partial stripping of most of the hydrogen chloride, the water from the aqueous hydrogen chloride reactant and the water that is formed during the course of the reaction (also referred to herein as "water of reaction"), from the reaction mixture is carried out and a distillation or stripping column is fed with the liquid phase from the stripper. The gas phase from the stripper, which contains most of the unreacted hydrogen chloride, the excess water from the aqueous hydrogen chloride reactant and the reaction by-product water from the reaction mixture, is conducted to a distillation column fed by the vapor produced by the reactor; or is recycled directly to the reactor.

The main fraction of dichloropropanol is collected from the top of the distillation or stripping column. The column residue is recycled to the reactor. This process (also referred to herein as a "wet process"), not only adds water via the aqueous hydrogen chloride reactant into the process, but also produces water of reaction in the process. The removal of a large excess of water in the wet process via a stripper is less energy efficient and unnecessary for a dry process. A better utilization of the stripper can be done in the recovery of dichloropropanol. This wet process also does not describe specific methods to minimize heavy by-product formation.

CN 101007751A describes another process that combines wet and dry processes with two reactors in series, in which a tubular reactor is used as the first reactor and a foaming-tank reactor is used as the second reactor. Aqueous hydrogen chloride is fed to the tubular reactor and gaseous hydrogen chloride is fed to the foaming-tank reactor. Inert impurities are added to the hydrogen chloride in order to improve the efficiency of stripping water from the reaction mixture in the foaming-tank reactor. CN 101007751A also does not describe specific methods to minimize heavy by-product formation.

EP 1 762 556 A1 describes a process for producing dichloropropanol by reacting a glycerol containing metal salt with a chlorinating agent in a reaction mixture. At least a fraction obtained from the reaction mixture, which contains metal salt, is subjected to a treatment comprising one or more separation operations to remove metal salt from said fraction. EP 1 762 556 A1 does not describe a process or an apparatus for reducing the formation of heavy byproducts during recovery of dichlorohydrins.

The inventor found that one or more component(s) of the reaction mixture fed to the distillation column according to the above processes form heavy byproducts during distillation requiring a purge from the process to prevent build up of the heavy byproducts in a continuous recycle process. WO 2005/021476 A1 describes processing a residue containing a mixture of undesired products but WO 2005/021476 A1 does not describe how to minimize formation of the undesired higher-boiling waste products during distillation. The heavy byproducts and the purge reduce recovery of dichlorohydrin(s) in a recycle process and increase cost related to non-utilizable byproduct waste disposal/conversion. Opportunities remain to further improve such distillation processes to reduce byproduct formation Accordingly, it is desired to provide improved processes and apparatus for separating the product dichlorohydrin from the reaction effluent of hydrochlorination of multi-hydroxylated aliphatic hydrocarbon compounds.

It is also desired to provide a process and apparatus whereby formation of the heavy byproducts such as various ethers of multi-hydroxylated aliphatic hydrocarbon compounds, chlorohydrins, and even higher molecular weight materials such as chlorinated oligomers is minimized.

SUMMARY OF THE INVENTION

One aspect of the present invention is a process reducing the formation of heavy byproducts during recovery of dichlorohydrin(s) from a reactive mixture containing the same comprising:
(a) providing a mixture comprising (1) dichlorohydrin(s), (2) one or more reactive components comprising (a') one or more ester(s) of chlorohydrin(s) and/or multihydroxylated-aliphatic hydrocarbon compound(s) and/or (b') one or more monochlorohydrin(s) and/or multihydroxylated-aliphatic hydrocarbon compound(s) in the presence of one or more ester(s) of chlorohydrin(s), ester(s) of multihydroxylated-aliphatic hydrocarbon compound(s), catalyst(s), and/or ester(s) of catalyst(s), and (3) optionally one or more substances comprising water, chlorinating agent(s), catalyst(s), ester(s) of catalyst(s), and/or heavy byproducts and
(b) distilling the mixture of step (a) in one or more liquid-vapor contacting devices having a total of at least 3 theoretical stages and an average pressure drop per theoretical stage not greater than 1.3 kPa to separate at least one distillate comprising dichlorohydrin(s) from the mixture provided in step (a).

One embodiment of the present invention includes the above process wherein the pressure difference between the first and last theoretical stages of the liquid-vapor contacting device is not greater than 7 kPa.

Another aspect of the present invention is a method for producing dichlorohydrin(s), wherein the mixture provided in step (a) is produced or derived from hydrochlorination of monochlorohydrin(s) and/or ester(s) thereof and/or multihydroxylated-aliphatic hydrocarbon compound(s) and/or ester(s) thereof.

Yet another aspect of the present invention is an apparatus suitable for producing dichlorohydrin(s) from multihydroxylated-aliphatic hydrocarbon compound(s) and/or ester(s) thereof comprising:
(1) at least one reactor;
(2) at least one separation device comprising one or more liquid-vapor contacting devices having a total of at least 3 theoretical stages and an average pressure drop per theoretical stage not greater than 1.3 kPa when the pressure at the highest theoretical stage of the liquid-vapor contacting device is less than or equal to 13 kPa and
(3) a means for applying vacuum to the at least one liquid-vapor contacting device of the at least one separation device (2) capable of reducing the pressure within the liquid-vapor contacting device to less than or equal to 13 kPa measured at the highest theoretical stage of the liquid-vapor contacting device
wherein
the at least one reactor (1) is connected either directly or indirectly to the at least one separation device (2) for conducting a reactor effluent stream from the at least one reactor (1) to the at least one liquid-vapor contacting device of the at least one separation device (2) for distillation.

One embodiment of the present invention includes the above apparatus wherein the pressure difference between the first and last theoretical stages of the liquid-vapor contacting device is not greater than 7 kPa.

DETAILED DESCRIPTION OF THE INVENTION

Definitions

As used herein, the term "multihydroxylated-aliphatic hydrocarbon compound" (abbreviated hereafter as "MAHC") refers to a compound that contains at least two hydroxyl groups covalently bonded to two separate vicinal carbon atoms and no ether linking groups. They contain at least two sp3 hybridized carbons each bearing an OH group. The MAHCs include any vicinal-diol (1,2-diol) or triol (1,2,3-triol) containing hydrocarbon including higher orders of contiguous or vicinal repeat units. The definition of MAHC also includes for example one or more 1,3-1,4-, 1,5- and 1,6-diol functional groups as well. Geminal-diols, for example, are precluded from this class of MAHCs.

The MAHCs contain at least 2, preferably at least 3, up to about 60, preferably up to 20, more preferably up to 10, even more preferably up to 4, and yet more preferably up to 3, carbon atoms and can contain, in addition to aliphatic hydrocarbon, aromatic moieties or heteroatoms including for example halide, sulfur, phosphorus, nitrogen, oxygen, silicon, and boron heteroatoms; and mixtures thereof. The MAHCs may also be a polymer such as polyvinyl alcohol.

The terms "glycerin", "glycerol" and "glycerine", and esters thereof, may be used as synonyms for the compound 1,2,3-trihydroxypropane, and esters thereof.

As used herein, the term "chlorohydrin" means a compound containing at least one hydroxyl group and at least one chlorine atom covalently bonded to two separate vicinal aliphatic carbon atoms and no ether linking groups. Chlorohydrins are obtainable by replacing one or more hydroxyl groups of MAHCs with covalently bonded chlorine atoms via hydrochlorination. The chlorohydrins contain at least 2, and preferably at least 3, up to about 60, preferably up to 20, more preferably up to 10, even more preferably up to 4, and yet more preferably up to 3, carbon atoms and, in addition to aliphatic hydrocarbon, can contain aromatic moieties or heteroatoms including for example halide, sulfur, phosphorus, nitrogen, oxygen, silicon, and boron heteroatoms, and mixtures thereof. A chlorohydrin that contains at least two hydroxyl groups is also a MAHC.

As used herein, the term "monochlorohydrin" means chlorohydrin having one chlorine atom and at least two hydroxyl groups, wherein the chlorine atom and at least one hydroxyl group are covalently bonded to two separate vicinal aliphatic carbon atoms (referred to hereafter by the abbreviation "MCH"). MCH produced by hydrochlorination of glycerin or glycerin esters includes, for example, 3-chloro-1,2-propanediol and 2-chloro-1,3-propanediol.

As used herein, the term "dichlorohydrin" means chlorohydrin having two chlorine atoms and at least one hydroxyl group, wherein at least one chlorine atom and at least one hydroxyl group are covalently bonded to two separate vicinal aliphatic carbon atoms (referred to hereafter by the abbreviation "DCH"). Dichlorohydrins produced by hydrochlorination of glycerin or glycerin esters include 1,3-dichloro-2-propanol and 2,3-dichloro-1-propanol.

As used herein, the expression "under hydrochlorination conditions" means conditions capable of converting at least 1 wt. %, preferably at least 5 wt. %, more preferably at least 10 wt. % of MAHCs, MCHs, and esters of MAHCs and MCHs present in a mixture and/or feed stream into DCH(s) and/or ester(s) thereof.

As used herein, the term "byproduct(s)" means compound(s) that is/are not chlorohydrin(s) and/or ester(s) thereof and/or chlorinating agent(s) and that do not form chlorohydrin(s) and/or ester(s) thereof under the hydrochlorinating conditions selected according to the present invention.

The expression "heavy byproduct(s)" refer to oligomers of mixture (a) components, such as oligomers of MAHCs and/or esters thereof and oligomers of chlorohydrins and/or esters thereof, and derivatives of such oligomers, such as esters thereof, chlorinated oligomers, and/or chlorinated esters thereof, having a number average molecular weight equal to or greater than the number average molecular weight of the oligomer, such as chlorinated oligomers. The terms chlorohydrin(s), MCH(s) and DCH(s), and ester(s) thereof, are not intended to include heavy byproducts.

The term "epoxide" means a compound containing at least one oxygen bridge on a carbon-carbon bond. Generally, the carbon atoms of the carbon-carbon bond are contiguous and the compound can include other atoms than carbon and oxygen atoms, like hydrogen and halogens, for example. Preferred epoxides are ethylene oxide, propylene oxide, glycidol and epichlorohydrin.

As used herein, the expression, "liquid phase" refers to a continuous intermediate phase between gas phase and a solid phase that may optionally comprise a minor amount of gas and/or solid discrete phase(s). The liquid phase may comprise one or more immiscible liquid phases and may contain one or more dissolved solids, such as one or more acids, bases, or salts.

As used herein, the expression "vapor phase" refers to a continuous gaseous phase that may optionally comprise a minor amount of liquid and/or solid discrete phase(s) (e.g., aerosol). The vapor phase may be a single gas or a mixture, such as a mixture of two or more gases, two or more liquid discrete phases, and/or two or more solid discrete phases.

The expression "lower boiling fraction" refers to a fraction derived from the mixture provided in step (a) in which more than half the total quantity of components of the lower boiling fraction are components of the mixture, or derived from the mixture, that are more volatile under the conditions of the unit operation than the components of the higher boiling fraction in the same unit operation derived from the same mixture provided in step (a).

The expression "higher boiling fraction" refers to a fraction derived from the mixture provided in step (a) in which more than half the total quantity of components of the higher boiling fraction are components of the mixture, or derived from the mixture, that are less volatile than the components of the lower boiling fraction in the same unit operation derived from the same mixture provided in step (a).

As used herein, the expression "liquid-vapor contacting device" refers to devices that serve to provide the contacting and development of at least one interfacial surface between liquid and vapor in the device. Examples of liquid-vapor contacting devices include plate column, packed column, wetted-wall (falling film) column, spray column, heat exchanger or any combination thereof. Examples of devices comprising plate columns and packed columns include distillation columns, fractionation columns, and stripping columns.

As used herein, the term "condenser" means a non-adiabatic system for removing heat from a process fluid via a secondary fluid physically separated from the process fluid. The process fluid and the secondary fluid may each be a vapor, a liquid, or a combination of liquid and vapor. A condenser is generally associated with a section of a distillation or fractionation liquid-vapor contacting device. It may be a unit operation external to a distillation column or it may be a unit operation internal to a distillation column. The physical separation may be in the form of tubes and the condensation may be carried out on the inside or outside of the tubes. The condenser may take the form of cooling elements on the decks of distillation column fractionating trays or as cooling elements between distillation column packing beds.

Mixture (a):

Mixture (a) may be obtained directly or indirectly from any hydrochlorination process well-known in the art. For example, German Patent No. 197308 teaches a process for preparing a chlorohydrin by the catalytic hydrochlorination of glycerin by means of anhydrous hydrogen chloride. WO 2005/021476 discloses a continuous process for preparing the dichloropropanols by hydrochlorination of glycerin and/or monochloropropanediols with gaseous hydrogen chloride with catalysis of a carboxylic acid. WO 2006/020234 A1 describes a process for conversion of a glycerol or an ester or a mixture thereof to a chlorohydrin, comprising the step of contacting a MAHC, an ester of a MAHC, or a mixture thereof with a source of a superatmospheric partial pressure of hydrogen chloride to produce a chlorohydrin, an ester of a chlorohydrin, or a mixture thereof in the presence of an organic acid catalyst without substantially removing water. The above references are hereby incorporated herein by reference with respect to the above-described disclosures.

In an exemplifying hydrochlorination process, MAHC and a hydrochlorination catalyst are charged to the hydrochlorination reactor. Then a chlorinating agent such as hydrogen chloride is added to the reactor. The reactor pressure is adjusted to the desired pressure and the reactor contents are heated to the desired temperature for the desired length of time. After completion of the hydrochlorination reaction or while carrying out the hydrochlorination reaction, the reactor contents as a reaction effluent stream is discharged from the reactor and fed directly, or indirectly via another reactor or other intervening step, to a separation system comprising a DCH recovery system according to the present invention and optionally including other separation systems or equipment, such as a flash vessel and/or reboiler.

The hydrochlorination reaction above may be carried out in one or more hydrochlorination reactor vessels such as a single or multiple continuous stirred tank reactors (referred to hereafter by the abbreviation "CSTR"), single or multiple tubular reactor(s), plug flow reactors (referred to hereafter by the abbreviation "PFR"), or combinations thereof. The hydrochlorination reactor can be, for example, one reactor or multiple reactors connected with each other in series or in parallel including, for example, one or more CSTRs, one or more tubular reactors, one or more PFRs, one or more bubble column reactors, and combinations thereof.

In a preferred embodiment, part or all of the hydrochlorination effluent stream is a feed stream from a PFR or a system of reactors which together simulate a plug flow characteristic. "Plug flow" refers to a flow pattern in a vessel or a system of vessels such that all elements of the fluid are moving through the vessel or the system of vessels at the same speed such that all fluid elements have the same residence time in the vessel or the system of vessels. The PFR is also called slug flow, piston flow, ideal tubular and unmixed flow reactor. There may be lateral mixing of fluid in a plug flow vessel but there should be no mixing or diffusion along the flow path. In practice, there is usually some backmixing and diffusion between the flow elements in the direction of the flow resulting in a deviation from an ideal plug flow but it closely approaches an ideal plug flow pattern. This is different from another type of reactor called a mixed reactor, a back-mixed reactor or a stirred tank reactor, also called continuous stirred tank reactor (CSTR) in which the vessel contents are well stirred and uniform throughout the vessel or the reactor, so that the exit stream from the latter has the same composition as the fluid within the reactor.

A PFR also has a composition profile in the reactor system. Concentration of the reactants being fed into the PFR decreases from inlet to the outlet along the flow path of the PFR and the concentration of products increases from inlet to the outlet along the flow path of the PFR. In the case of hydrochlorination of glycerol, the concentration of HCl and glycerol decreases from inlet of the PFR to outlet of the PFR while the total concentration of 1,3-dichloro-2-propanol and 2,3-dichloro-1-propanol increases from inlet of the PFR to the outlet of the PFR.

The equipment useful for conducting the hydrochlorination reaction may be any well-known equipment in the art and should be capable of containing the reaction mixture at the conditions of the hydrochlorination. Suitable equipment may be fabricated of materials which are resistant to corrosion by the process components, and may include for example, metals such as tantalum, suitable metallic alloys (particularly nickel-molybdenum alloys such as Hastalloy C©), or glass-lined equipment, for example.

In addition to DCH(s), one or more of the unreacted MAHC(s) and/or chlorination agent(s), reaction intermediates such as MCH(s), MCH ester(s), and/or DCH ester(s), catalyst(s), ester(s) of catalyst(s), water, and/or heavy byproduct(s) may present in mixture (a). A recycle process is preferred in which one or more of the unreacted MAHC(s), ester(s) of MAHC(s) and/or chlorination agent(s), reaction intermediates such as MCH(s), MCH ester(s), DCH ester(s), and other substances such as catalyst(s), ester(s) of catalyst(s), and water are preferably recycled to a prior step in the process, such as to at least one hydrochlorination reactor for further hydrochlorination. In particular, a liquid higher boiling fraction comprising a residue of the distilling or fractionating step containing one or more of MAHC(s), MCH(s), catalyst(s), and/or ester(s) of one or more MAHC(s), MCH(s), DCH(s) and/or catalyst(s), and preferably a combination of two or more thereof, is recycled to the hydrochlorination step, such as by recycling the higher boiling fraction to one or more reactor(s), Such recycle process(es) is preferably continuous. In this manner, raw material efficiencies are maximized and/or catalysts are reused.

When catalysts are reused in such a process scheme, it may be desirable to employ the catalysts in a higher concentration than they are employed in a single-pass process. This may result in faster reactions, or smaller process equipment, which results in lower capital costs for the equipment employed.

In a continuous recycle process, undesirable impurities and/or reaction byproducts may build up in the process. Thus, it is desirable to provide a means for removing such impurities from the process, such as via one or more purge outlets, for example, or by a separation step. Furthermore, a purged stream may be further treated to recover a useful portion of the purged stream.

The chlorinating agent that may optionally be present in the mixture treated according to the present invention is preferably hydrogen chloride or hydrogen chloride source, and may be a gas, a liquid or in a solution, or a mixture thereof. The hydrogen chloride is preferably introduced in the gaseous state and, when the hydrochlorination reaction mixture is in the liquid phase, at least some of the hydrogen chloride gas is preferably dissolved in the liquid reaction mixture. The hydrogen chloride may, however, be diluted in a solvent, such as an alcohol (for example methanol), or in a carrier gas such as nitrogen, if desired.

It is preferred that the hydrochlorination step of the present invention be carried out under superatmospheric pressure conditions. "Superatmospheric pressure" herein means that the hydrogen chloride (HCl) partial pressure is above atmospheric pressure, i.e. 15 psia (103 kPa) or greater. Generally, the hydrogen chloride partial pressure employed in the hydrochlorination process is at least about 15 psia (103 kPa) or greater. Preferably, the hydrogen chloride partial pressure employed in the hydrochlorination process is not less than about 25 psia (172 kPa), more preferably not less than about 35 psia (241 kPa), and most preferably not less than about 55 psia (379 kPa); and preferably not greater than about 1000 psia (6.9 MPa), more preferably not greater than about 600 psia (4.1 MPa), and most preferably not greater than about 150 psia (1.0 MPa).

It is also preferred to conduct the hydrochlorination step at a temperature sufficient for hydrochlorination that is also below the boiling point of the chlorohydrin(s) in the reaction mixture having the lowest boiling point for a given pressure condition during the hydrochlorination step in order to keep the chlorohydrin(s) produced and converted during hydrochlorination in the liquid phase of the reaction mixture for recovery in steps (b) and (c). The upper limit of this preferred temperature range may be adjusted by adjusting the pressure condition. A higher pressure during hydrochlorination may be selected to increase the boiling point temperature of the chlorohydrin(s) in the reaction mixture, so that the preferred temperature range for keeping DCH(s) in the liquid phase may be increased by increasing the pressure condition.

Preferably, less than 50, more preferably less than 10, even more preferably less than 5, and yet more preferably less than 1, percent of the DCH present in the hydrochlorination effluent is removed from the hydrochlorination effluent prior to step (b).

The hydrochlorination effluent comprises one or more DCHs, one or more compounds comprising ester(s) of DCH(s), MCH(s) and/or ester(s) thereof, and MAHC(s) and/or ester(s) thereof, and optionally one or more substances comprising water, chlorination agent(s), catalyst(s) and/or ester(s) of catalyst(s). Additional optional components may also be present in the effluent depending on the starting materials, reaction conditions, and any process steps intervening between the hydrochlorination reaction and recovery of DCH according to the present invention. The hydrochlorination effluent is preferably in the liquid phase as the hydrochlorination effluent is withdrawn from the hydrochlorination step and/or reactor and the mixture provided in step (a) comprises at least part of the liquid phase effluent of the hydrochlorination step.

In a preferred embodiment, at least one MAHC and/or ester thereof is present in the mixture provided in step (a). When MAHC(s) and/or ester(s) thereof is/are present in the mixture provided in step (a), the same MAHC(s) and/or ester(s) thereof may also be present in the high-boiling fraction of step (b).

MAHCs found in the effluent treated according the present invention may include for example 1,2-ethanediol; 1,2-propanediol; 1,3-propanediol; 3-chloro-1,2-propanediol; 2-chloro-1,3-propanediol; 1,4-butanediol; 1,5-pentanediol; cyclohexanediols; 1,2-butanediol; 1,2-cyclohexanedimethanol; 1,2,3-propanetriol (also known as, and used herein interchangeable as, "glycerin", "glycerine", or "glycerol"); and mixtures thereof. Preferably, the MAHCs in the effluents treated according to the present invention include for example 1,2-ethanediol; 1,2-propanediol; 1,3-propanediol; and 1,2,3-propanetriol; with 1,2,3-propanetriol being most preferred.

Examples of esters of MAHCs found in the effluents treated according to the present invention include for example ethylene glycol monoacetate, propanediol monoacetates, glycerin monoacetates, glycerin monostearates, glycerin diacetates, and mixtures thereof. In one embodiment, such esters can be made from mixtures of MAHC with exhaustively esterified MAHC, for example mixtures of glycerol triacetate and glycerol.

In the same or another preferred embodiment, at least one MCH and/or ester thereof is present in the mixture provided in step (a). When MCH(s) and/or ester(s) thereof is/are present in the mixture provided in step (a), the same MCH(s) and/or ester(s) thereof may also be present in the high-boiling fraction of step (b).

The MCHs generally correspond to the hydrochlorinated MAHCs in which one of a pair of hydroxyl groups covalently bonded to two separate vicinal carbon atoms is replaced by a covalently bonded chlorine atom. The ester(s) of MCH may be the result of hydrochlorination of MAHC ester(s) or reaction with an acid catalyst, for example.

The DCHs generally correspond to the hydrochlorinated MAHCs in which two hydroxyl groups covalently bonded to two separate carbon atoms, at least one of which is vicinal to a third carbon atom having a hydroxyl group, are each replaced by a covalently bonded chlorine atom. The ester(s) of DCH(s) may be the result of hydrochlorination of MAHC ester(s), MCH ester(s) or reaction(s) with acid catalyst(s), for example.

In an embodiment of the present invention where MAHC(s) is/are the starting material fed to the process, as opposed to ester(s) of MAHC(s) or a mixture of MAHC(s) and ester(s) thereof as a starting material, it is generally preferred that the formation of chlorohydrin be promoted by the presence of one or more catalyst(s) and/or ester(s) thereof. Catalyst(s) and/or ester(s) thereof may also be present where ester(s) of MAHC(s), or a mixture of MAHC(s) and ester(s) thereof, is a starting material to further accelerate the hydrochlorination reaction.

Carboxylic acids, RCOOH, catalyze the hydrochlorination of MAHCs to chlorohydrins. The specific carboxylic acid catalyst chosen may be based upon a number of factors including for example, its efficacy as a catalyst, its cost, its stability to reaction conditions, and its physical properties. The particular process, and process scheme in which the catalyst is to be employed may also be a factor in selecting the particular catalyst. The "R" groups of the carboxylic acid may be independently chosen from hydrogen or hydrocarbyl groups, including alkyl, aryl, aralkyl, and alkaryl. The hydrocarbyl groups may be linear, branched or cyclic, and may be substituted or un-substituted. Permissible substituents include any functional group that does not detrimentally interfere with the performance of the catalyst, and may include heteroatoms. Non-limiting examples of permissible functional groups include chloride, bromide, iodide, hydroxyl, phenol, ether, amide, primary amine, secondary amine, tertiary amine, quaternary ammonium, sulfonate, sulfonic acid, phosphonate, and phosphonic acid.

The carboxylic acids useful as hydrochlorination catalysts may be monobasic such as acetic acid, formic acid, propionic acid, butyric acid, isobutyric acid, hexanoic acid, 4-methylvaleric acid, heptanoic acid, oleic acid, or stearic acid; or polybasic such as succinic acid, adipic acid, or terephthalic acid. Examples of aralkyl carboxylic acids include phenylacetic acid and 4-aminophenylacetic acid. Examples of substituted carboxylic acids include 4-aminobutyric acid, 4-dimethylaminobutyric acid, 6-aminocaproic acid, 6-hydroxyhexanoic acid, 6-chlorohexanoic acid, 6-aminohexanoic acid, 4-aminophenylacetic acid, 4-hydroxyphenylacetic acid, lactic acid, glycolic acid, 4-dimethylaminobutyric acid, and 4-trimethylammoniumbutyric acid. Additionally, materials that can be converted into carboxylic acids under reaction conditions, including for example carboxylic acid halides, such as acetyl chloride, 6-chlorohexanoyl chloride, 6-hydroxyhexanoyl chloride, 6-hydroxyhexanoic acid, and 4-trimethylammonium butyric acid chloride; carboxylic acid anhydrides such as acetic anhydride and maleic anhydride; carboxylic acid esters such as methyl acetate, methyl propionate, methyl pivalate, methyl butyrate, ethylene glycol monoacetate, ethylene glycol diacetate, propanediol monoacetates, propanediol diacetates, glycerin monoacetates, glycerin diacetates, glycerin triacetate, and glycerin esters of a carboxylic acid (including glycerin mono-, di-, and tri-esters); MAHC acetates such as glycerol 1,2-diacetate; carboxylic acid amides such as ε-caprolactam and γ-butyrolactam; and carboxylic acid lactones such as γ-butyrolactone, δ-valerolactone and ε-caprolactone may also be employed in the present invention. Zinc acetate is an example of a metal organic compound. Mixtures of the foregoing catalysts and catalyst precursors may also be used.

When a catalyst is used in the superatmospheric pressure process, the catalyst may be for example a carboxylic acid; an anhydride; an acid chloride; an ester; a lactone; a lactam; an amide; a metal organic compound such as sodium acetate; or a combination thereof. Any compound that is convertible to a carboxylic acid or a functionalized carboxylic acid under hydrochlorination reaction conditions may also be used. A preferred carboxylic acid for the superatmospheric pressure process is an acid with a functional group consisting of a halogen, an amine, an alcohol, an alkylated amine, a sulfhydryl, an aryl group or an alkyl group, or combinations thereof, wherein this moiety does not sterically hinder the carboxylic acid group.

Certain catalysts may also be advantageously employed at superatmospheric, atmospheric or sub-atmospheric pressure, and particularly in circumstances where water is continuously or periodically removed from the reaction mixture to drive conversion to desirably higher levels as may be the case when recovering DCH(s) according to the claimed invention. For example, the hydrochlorination of MAHC(s) reaction can be practiced by introducing hydrogen chloride gas into contact with a mixture of MAHC(s) and catalyst(s), such as by sparging the hydrogen chloride gas through a liquid phase reaction mixture. In such a process, the use of less volatile catalysts, such as 6-hydroxyhexanoic acid, 4-aminobutyric acid; dimethyl 4-aminobutyric acid; 6-chlorohexanoic acid; caprolactone; carboxylic acid amides such as ε-caprolactam and γ-butyrolactam; carboxylic acid lactones such as γ-butyrolactone, δ-valerolactone and ε-caprolactone; caprolactam; 4-hydroxyphenyl acetic acid; 6-amino-caproic acid; 4-aminophenylacetic acid; lactic acid; glycolic acid; 4-dimethylamino-butyric acid; 4-trimethylammoniumbutyric acid; and combination thereof; and the like may be preferred. It is most desirable to employ a catalyst, under these atmospheric or subatmospheric conditions, that is less volatile than the DCH(s) produced and recovered.

Preferred catalysts used in the present invention include carboxylic acids, esters of carboxylic acids, and combinations thereof, particularly esters and acids having a boiling point higher than that of the desired highest boiling DCH that is formed in the reaction mixture (i.e., the catalyst(s) is/are preferably less volatile than the DCH(s) in the mixture), so that the DCH(s) can be removed without removing the catalyst. Catalysts which meet this definition and are useful in the present invention include for example, polyacrylic acid, glycerin esters of carboxylic acids (including glycerin mono-, di-, and tri-esters), polyethylene grafted with acrylic acid, divinylbenzene/methacrylic acid copolymer, 6-chlorohexanoic acid, 4-chlorobutanoic acid, caprolactone, heptanoic acid, 4-hydroxyphenylacetic acid, 4-aminophenylacetic acid, 6-hydroxyhexanoic acid, 4-aminobutyric acid, 4-dimethylaminobutyric acid, 4-trimethyl-ammoniumbutyric acid chloride, stearic acid, 5-chlorovaleric acid, 6-hydroxyhexanoic acid, 4-aminophenylacetic acid, and mixtures thereof. Carboxylic acids that are sterically unencumbered around the carboxylic acid group are generally preferred.

Furthermore, the catalyst(s) is/are preferably miscible with the MAHC(s) employed. For this reason, the catalyst(s) may contain polar heteroatom substituents such as hydroxyl, amino or substituted amino, or halide groups, which render the catalyst miscible with the MAHC(s) in the reaction mixture, such as glycerol.

One embodiment of the catalyst(s) that may be present is generally represented by Formula (a) shown below wherein the functional group "R'" includes a functional group comprising an amine, an alcohol, a halogen, a sulfhydryl, an ether; or an alkyl, an aryl or alkaryl group of from 1 to about 20 carbon atoms containing said functional group; or a combination thereof; and wherein the functional group "R" may include a hydrogen, an alkali, an alkali earth or a transition metal or a hydrocarbon functional group.

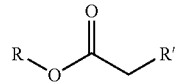

Formula (a)

Where the catalyst is recycled and used repeatedly, such recycled catalysts may be present in an amount from about 0.1 mole %, preferably from about 1 mole %, more preferably from about 5 mole %, up to about 99.9 mole %, preferably up to 70 mol %, and more preferably up to 50 mole %, based on the amount in moles of MAHC present. Higher catalysts concentrations may be desirably employed to reduce the reaction time and minimize the size of process equipment.

In a preferred embodiment, the mixture (a) comprises water, such as the water produced as a byproduct of the hydrochlorination reaction, water present in the starting materials for the hydrochlorination reaction, and/or water introduced as the stripping agent. The mixture (a) may contain at least 1, or at least 5, weight-percent water up to 90, more preferably up to 50, even more preferably up to 20, and most preferably up to 10 weight-percent water.

The mixture of step (a) may be a liquid phase or a combination of liquid phase and vapor phase. In one embodiment, the mixture of step (a) is provided to step (b) by separating a hydrochlorination reaction effluent stream into a vapor-phase effluent stream and a liquid-phase effluent stream prior to step (b) and introducing the liquid-phase effluent stream or both the vapor-phase effluent stream and the liquid-phase effluent streams, separately or combined, into step (b). The separation of the reaction effluent stream may be carried out in, for example, in a separation system comprising a liquid-vapor contacting device and, optionally, with a flash vessel separate from or integral with liquid-vapor contacting device in step (b).

Recovery of DCH from the Mixture (a):

Recovering DCH(s) from the mixture comprises distilling or fractionating the mixture under reflux conditions to separate from the mixture a first vapor phase effluent stream comprising one or more of the above-identified DCH(s) and water having a first temperature equal to or greater than the boiling point of the DCH(s) and water present in the mixture at the pressure of the first vapor phase effluent. The DCH(s) preferably comprise(s) 1,3-dichloro-2-propanol and/or 2,3-dichloro-1-propanol), and ester(s) thereof.

The first vapor phase effluent stream may contain one or more of the above-identified MCH(s), such as 2-chloro-1,3-propanediol and/or 3-chloro-1,2-propanediol, and ester(s) thereof; one or more of the above-identified MHAC(s); and/ or one or more of the above-identified substances comprising chlorinating agent(s), catalyst(s), and/or ester(s) of catalyst(s). Distilling or fractionating step (a) enriches the concentration of DCH(s) in the first vapor phase effluent stream relative to the mixture fed to the distilling or fractionating step.

Distillation or fractionation step (b) is preferably carried out at a temperature measured in the distillation bottoms of at least 25° C., more preferably at least 50° C., yet more preferably at least 80° C., even more preferably at least 100° C., and yet even more preferably at least 110° C., up to 160° C., preferably up to 150° C., even more preferably up to 140° C., yet even more preferably up to 130° C., and most preferably up to 120° C.

Milder separation conditions may include reducing the temperature of the distillation bottoms to reduce the rate of heavy byproduct formation during step (b). Safety and efficiency of the process are improved when the distillation column is operated at a lower bottom temperature. The lower bottom temperature also reduces the risk of a run away reaction in the case of a process upset such as loss of vacuum or loss of power to the plant.

One method of achieving low temperature in the bottom of the column is operating the column under a vacuum condition such that the pressure in the top of the column is maintained less than 100 kPa, preferably less than 50 kPa, more preferably less than 10 kPa, even more preferably less than 5 kPa and most preferably less than 2 kPa and greater than 0.1 kPa, preferably greater than 0.5 kPa and most preferably greater than 1 kPa. Lower pressure in the column helps achieve lower temperature in the bottom of the column, but this must be balanced with increased column size as well as increased operating cost required at lower pressures. Increased column size results in increased capital cost of the column and the column internals.

Step (b) is preferably carried out in a distillation column, such as a fractional distillation column. Examples of suitable distillation columns include plate or tray columns, bubble cap columns, packed columns, and the like.

The at least one liquid-vapor contacting device is preferably a packed distillation column. The columns that have packing elements inside them for gas-liquid contacting are called packed columns. The packed columns are usually filled with a randomly oriented packing material by dumping the packing elements into the column and allowing them to form a random arrangement of packing forming a packed bed. Many types of random packings are commercially available and several types are in common use. Some of the commercially available random packings are raschig ring, berl saddles, tellerette, pall rings, intalox saddles, IMTP and the like. Alternatively, larger sections of rigid, or arranged packing material, called structured packing, may be inserted carefully into the column. Random packing is usually cheaper. Structured (ordered, arranged, or stacked) packing may be made of for example, knitted wire, corrugated and perforated sheets. Some of the commercially available structured packing are Koch Flexipac, Sulzer Mellapak, Koch BX and the like. The packing or internals used in the process and equipment of the present invention are preferably made of an appropriate material of construction to provide resistance against corrosion and provide good liquid-wet ability.

Another aspect of achieving low temperature in the bottom of the column is minimizing pressure drop in the column or columns. Pressure drop in a column such as a distillation column depends on the type of internals used in the column. Type of internals used in the column must be such that they require minimum pressure drop per theoretical equilibrium stage. Packed columns have lower pressure drop per theoretical stage than plate or tray columns. The packing selected for the packed column(s) should have one of the lowest pressure drops per theoretical stage available. Structured packings have a lower pressure drop per theoretical stage than random packings. Therefore, structured packing is one preferred optional embodiment of the present invention.

The average pressure drop between the first and last theoretical stage during step (b) is not greater than 1.3 kPa, preferably not greater than 1 kPa, more preferably not greater than 0.7 kPa, and even more preferably not greater than 0.4 kPa, per theoretical stage.

Theoretical equilibrium stage, more often called theoretical stage, is a well-established principle in the field of chemical engineering for, more particularly in the field of distillation. Perry's Chemical Engineers' Handbook, $7^{th}$ edition, page 13-4 defines a theoretical equilibrium stage. The number of theoretical equilibrium stages required is then converted to an equivalent number of actual contact trays or height of packing. In a column with trays, actual tray efficiency is always less than 100%, resulting in requiring more trays than theoretical stages.

It is also important to not install more than required number of stages in the column to minimize total pressure drop in the column i.e. pressure difference between the first and the last theoretical stage of the column. Minimizing packing height in a packed column minimizes pressure drop in the column. The total pressure drop in the column should not be greater than 7 kPa, preferably not greater than 5 kPa and more preferably not greater than 3 kPa.

The number of required theoretical equilibrium stages depends on the components to be separated, their relative volatility and also the degree of desired separation between the light and the heavy key components. In a preferred embodiment of this invention, 1-MCH is the heavy key which, in other words, is the key heavy component of interest in the distillate whereas 1,3-DCH is the, key light component of interest in the column bottoms, making it a light key. In a preferred embodiment of the invention, concentration of 1-MCH in the distillate desired is less than 1 wt. %, preferably less than 0.1 wt %, more preferably less than 500 ppm by wt. and most preferably less than 100 ppm. by wt. Achieving very low concentration of DCH (including both 1,3-DCH and 2,3-DCH) in the bottom of the column is less critical in a continuous recycle process because overall recovered DCH yield is not affected significantly by this. Of course, it is desired to have concentration of DCH as low as possible in the column bottoms to minimize equipment size but doing so results in increased temperature in the bottom which results in grater rate of heavy byproducts formation in the bottom. It is desired to minimize this heavy byproducts formation rate by minimizing temperature in the bottom of the column.

Therefore, another embodiment of the process of this invention is maintaining sufficient concentration of DCH in the column bottoms to achieve the desired temperature in the column bottom at the selected pressure. Total DCH concentration in the column bottoms should be at least 1 weight percent, preferably at least 5 weight percent, more preferably at least 10 weight percent, even more preferably at least 15 weight percent; and up to 30 weight percent, and preferably less than 25 weight percent.

In another embodiment of the present invention, steam stripping may be employed for the desired separation which allows operating the column at a higher pressure while keeping the process material at relatively low temperatures. The higher pressure condition process allows for energy savings and a wider selection of vacuum devices. A more economical steam-jet ejector or vacuum pump can be used, which reduces fixed capital and operating costs. Operational reliability is also improved through the use of steam-jet ejectors, because steam-jet ejectors do not have moving parts, while low pressure, high vacuum operation generally requires the use of rotary oil-sealed vacuum pumps or multiple stages of steam-jet ejectors. Also higher distillation column pressure operation reduces column size, thereby reducing the capital investment to be amortized.

The percent DCH(s) recovered from the mixture introduced into step (b) generally depends on the combination of temperature and pressure conditions selected. To obtain a given DCH recovery in step (b), a reduction in temperature generally requires a reduction in operating pressure and, conversely, an increase in operating pressure, requires an increase in operating temperature. The specific temperature and pressure conditions selected will depend on the extent to which realization of the respective benefits relating to low temperature and higher pressure operation is desired.

Step (b) is preferably carried out under conditions such that the amount of heavy byproducts in the high boiling fraction of step (b) does not exceed 120 percent, more preferably does not exceed 110 percent, even more preferably does not exceed 105 percent, most preferably does not exceed 102 percent of the amount of heavy byproducts in the mixture provided in step (a). Minimizing the heavy and undesired byproducts formation in the process allows reducing the process purge required to prevent buildup of heavy byproducts in the process when operating the process as a continuous recycle process. The purge stream may contain usable components in the process such as dichlorohydrins, monochlorohydrins, MAHCs, catalyst, and/or their esters. Therefore, minimizing the purge results in an increased yield of dichlorohydrins.

The mixture provided in step (a) may be passed through a pressure letdown step prior to distilling and/or fractionating the mixture such as via an intervening flash vessel, to reduce the pressure and flashing tendency of the mixture during distillation or fractionation. The flash vessel may act also as a surge or a buffer vessel to reduce the impact of flow fluctuations or surges upstream from the distillation and/or fractionation step, and help regulate the flow of the mixture into the distillation and/or fractionation step.

In one embodiment, additional MAHC(s) and/or ester(s) thereof may be introduced into step (b) for reactive distillation/fractionation. The additional MAHC(s) and/or ester(s) thereof may react with the chlorination agent to produce additional MCH(s) and/or ester(s) thereof. Additional MAHC(s) may also react with ester(s) of DCH(s) and MCH(s) to convert them to non-ester(s) to facilitate recovery of DCH(s). The additional MAHC(s) and/or ester(s) thereof is/are preferably introduced as a liquid phase into a reflux.

The above process steps may be carried out independently or simultaneously with one another. In a preferred embodiment, one or more of the above process steps is carried out simultaneously with one another.

One or more of the above process steps may be carried out continuously or discontinuously. One or more of the above process steps are preferably carried out continuously (i.e., without interruption) for a time period of at least one hour. Preferably, all the above process steps are carried out continuously for a time period of at least one hour.

At least some of the higher boiling fraction treated in step (b) is preferably recycled to a hydrochlorination step. In a more preferred embodiment, substantially all the higher boiling fraction treated in step (b) is recycled to a hydrochlorination step. The hydrochlorination step is preferably the first step in the hydrochlorination process used to produce a hydrochlorination effluent containing components of the mixture (a).

Recycling the treated higher boiling fraction permits further reaction of MAHC(s) and/or ester(s) thereof and/or MCH(s) and/or ester(s) thereof to form additional DCH, which generally increases the overall hydrochlorination conversion and recovery rates. In that case, the process according to the present invention may recover at least 80 percent, more preferably at least 90 percent, even more preferably at least 95 percent, yet more preferably at least 99 percent, and yet even more preferably at least 99.9 percent of the DCH(s) produced during hydrochlorination in step (a).

The at least one separation device (2) is preferably connected to the at least one reactor (1) for conducting a distillation residue effluent stream from the at least one liquid-vapor contacting device of the at least one separation device (2) to the at least one reactor (1) for recycling the distillation residue.

The at least one separation device preferably comprises a flash vessel connected between the at least one reactor (1) and the at least one liquid-vapor contacting device for separating a reactor effluent stream into a vapor-phase reactor effluent stream and a liquid-phase reactor effluent stream and for conducting both the liquid-phase effluent and the vapor phase effluent to the at least one liquid-vapor contacting device.

The following examples are for illustrative purposes only and are not intended to limit the scope of the present invention.

Equipment Used in the Examples

Distillation is carried out using a glass distillation column packed with 6 mm ceramic Intalox saddles, containing two packed bed sections. Feed to the column is located between the two packed bed sections. The column is provided with a glass reboiler and two partial condensers in series, also made of glass, for cooling the vapor stream exiting the column. The first condenser is cooled with chilled glycol. A portion of the condensate from the first condenser is returned to the column as reflux and the rest of the condensate is collected as product.

Uncondensed vapors from the first condenser are condensed in the second condenser operating at a lower temperature and cooled with chilled glycol. The uncondensed vapors exiting the second condenser are passed through a set of cold traps before entering the vacuum pump which provides vacuum to the whole system. The second condensed liquid-phase effluent from the second condenser is collected as product.

Example 1

In this example, a DCH recovery process is conducted according to the present invention based on the feed composition and conditions shown below in Table 1:

TABLE 1

| Distillation Column Process Conditions | | Units |
|---|---|---|
| Pressure at the top of the column | 1.6 | kPa |
| Temperature at the top of the column | 50 | ° C. |
| Pressure at the bottom of the column | 2.9 | kPa |
| Temperature at the bottom of the column | 113 | ° C. |
| Pressure drop across the column | 1.3 | kPa |

The distillation data is shown in Table 2:

TABLE 2

| Subject | Feed | Vent | Total Top Product | Bottom Product | Units |
|---|---|---|---|---|---|
| FlowRate | 2.534 | balance | 1.018 | 1.468 | kg/hr |
| $H_2O$ | 8.9 | | 21.2 | 0 | wt. % |
| HCl | 3.3 | | 7.6 | 0 | wt. % |
| 1,3-dichloro-2-propanol | 33.1 | | 69.5 | 7.4 | wt. % |
| 2,3-dichloro-1-propanol | 7.1 | | 1.8 | 11.0 | wt. % |
| 3-chloro-1,2-propanediol | 8.1 | | — | 15.7 | wt. % |
| 2-chloro-1,3-propanediol | 12.2 | | — | 21.0 | wt. % |
| glycerine | 15.6 | | — | 25.0 | wt. % |
| Heavies | 7.5 | | | 12.6 | wt % |
| other components | 4.2 | | 0 | 7.3 | wt. % |

Table 2 above shows that the stream comprising dichlorohydrins was separated into a top product stream comprising primarily dichlorohydrins and a bottom product stream comprising the heavier components in the feed stream such as monochlorohydrins, glycerol and other components which include the catalyst and its esters, ethers and higher molecular weight compounds without measurable formation of heavies. The measurements provided in Table 2 above are within acceptable experimental measurement error (relative) of about +/−5 percent to those skilled in the art.

The rate of byproduct formation in the overall continuous recycle process (not shown in Table 2) was less than 2 percent of the amount of DCH produced in the process.

Examples 2 to 4 and Comparative Examples A to C

Further examples presented below are based on process simulation of the distillation column. The distillation process model results compared well with experimental data. This process model was used to simulate effect of pressure drop in the column and its effect on temperature at the bottom of the column. Temperature at the bottom of the column depends on pressure at top of the column, pressure drop in the column as well as the composition of the process material at the bottom of the column as shown in the examples below. Example 3 illustrates the effect of increased temperature at the column bottom as a result of decrease in the dichlorohydrins concentration when compared with Example 2. Example 4 illustrates the effect of increased temperature at the column bottom as a result of increased pressure drop in the column when compared with Example 2. Comparative examples A-C illustrate the effect of further increase in pressure drop in the column when the column type is changed from packed to plate. The result is an increased temperature in the bottom of the column. This higher temperature in the bottom of the column results in greater rate of formation of high molecular weight material in the process which is an yield loss to the process and also leads to greater disposal cost because of the increased purge rate from the process to control build up of heavies in the process.

The computer simulation generated the distillation data shown in Table 3:

TABLE 3

| | Example 2 | Example 3 | Example 4 | Comparative Example A | Comparative Example B | Comparative Example C |
|---|---|---|---|---|---|---|
| Column type | Packed | Packed | Packed | Plate | Plate | Plate |
| Total theoretical stages including condenser and reboiler | 7 | 7 | 7 | 7 | 7 | 7 |
| Feed stage (above-stage) | 5 | 5 | 5 | 5 | 5 | 5 |
| Reflux ratio | 0.33 | 0.33 | 0.33 | 0.33 | 0.33 | 0.33 |
| Pressure at top of the column, mmHg | 10 | 10 | 10 | 10 | 10 | 10 |
| Pressure drop across the column, mmHg | 10 | 10 | 20 | 50 | 50 | 100 |
| Pressure at bottom of the column, mmHg | 20 | 20 | 30 | 60 | 60 | 110 |
| Dichlorohydrins in the bottom of the column, wt % | 10 | 4.8 | 10 | 10 | 4.8 | 20 |
| Temperature at bottom of the column, C. | 116 | 126 | 126 | 144 | 153 | 149 |

What is claimed is:

1. A process for reducing the formation of heavy byproducts during recovery of dichlorohydrin(s) from a reactive mixture including dichlorohydrin(s) comprising:
   (a) providing a mixture comprising (1) dichlorohydrin(s); (2) one or more reactive components comprising (a') one or more ester(s) of chlorohydrin(s) and/or multihydroxylated-aliphatic hydrocarbon compound(s), and/or (b') one or more monochlorohydrin(s) and/or multihydroxylated-aliphatic hydrocarbon compound(s) in the presence of one or more ester(s) of chlorohydrin(s), ester(s) of multihydroxylated-aliphatic hydrocarbon compound(s), catalyst(s), and/or ester(s) of catalyst(s); and (3) optionally, one or more substances comprising water, chlorinating agent(s), catalyst(s), ester(s) of catalyst(s), and/or heavy byproducts; wherein the catalyst(s) and/or ester(s) of catalyst(s) is selected from the group consisting of a carboxylic acid, an anhydride; an acid chloride; an ester; a lactone; a lactam; an amide; a metal organic compound, a metal salt, a compound convertible to a carboxylic acid under the reaction conditions of the process, and a combination thereof;
   (b) distilling the mixture provided in step (a) in a liquid-vapor contacting device having at least 3 theoretical stages to separate at least one distillate comprising dichlorohydrin(s) from the mixture provided in step (a); wherein the temperature in the bottom of the liquid-vapor contacting device is not greater than 150° C.;

(c) maintaining the pressure at the highest theoretical stage in the liquid-vapor contacting device such that the pressure is not greater than 5 kPa;
(d) maintaining the average pressure drop per theoretical equilibrium stage in the liquid-vapor contacting device such that the average pressure drop is not greater than 0.7 kPa, or such that the total pressure drop in the liquid-vapor contacting device is not greater than 5 kPa; and
(e) maintaining the concentration of dichlorohydrins, in the bottom of the liquid-vapor contacting device, to at least 5 weight percent;
wherein the formation of heavy (low volatility) byproducts during recovery of dichlorohydrin(s) from the mixture is reduced.

2. The process according to claim 1, wherein the total pressure drop in the liquid-vapor contacting device is not greater than 3 kPa; wherein the liquid in the bottom of the liquid-vapor contacting device comprises at least 10 weight percent dichlorohydrins; and wherein the temperature in the bottom of the liquid-vapor contacting device is not greater than 140° C.

3. The process according to claim 1, wherein the total pressure drop in the liquid-vapor contacting device is not greater than 3 kPa; wherein the bottom of the liquid vapor contacting device contains at least 15 weight percent dichlorohydrins; and wherein the temperature of the liquid in the bottom of the liquid-vapor contacting device during step (b) is not greater than 130° C.

4. The process according to claim 1, wherein the average pressure drop between the first and last theoretical stage during step (b) is not greater than 0.4 kPa per theoretical stage.

5. The process according to claim 1, wherein the mixture of step (a) comprises catalyst(s) and/or esters thereof; and wherein the catalyst is at least one carboxylic acid, at least one ester of at least one carboxylic acid, or a combination thereof, having a boiling point under the conditions of step (b) that is greater than the boiling point of the highest boiling dichlorohydrin under the conditions of step (b); or the catalyst (i) is a carboxylate a carboxylic acid or a compound convertible to a carboxylic acid under the reaction conditions of the process having from two to about 20 carbon atoms and having at least one functional group selected from the group consisting of an amine, an alcohol, a halogen, a sulthydryl, an ether, an ester, and a combination thereof, wherein the functional group is attached no closer to the acid function than the alpha carbon; (ii) is less volatile than the dichlorohydrin(s); and (iii) has heteroatom substituents.

6. The process according to claim 1, wherein the amount of heavy byproduct(s) in the distillation residue of step (b) does not exceed 120 percent of the amount of heavy byproduct in the mixture provided in step (a).

7. The process according to claim 1, wherein dichlorohydrin(s) is/are recovered from a distillate of step (b); and/or (ii) wherein a distillate produced in step (b) is subjected to epoxidation to form epichlorohydrin without additional purification of the distillate.

8. The process according to claim 1, wherein the mixture provided in step (a) is produced from hydrochlorination of monochlorohydrin(s) and/or ester(s) thereof and/or multihydroxylated-aliphatic hydrocarbon compound(s) and/or ester(s) thereof; and the mixture provided in step (a) comprises the liquid phase of the hydrochlorination step.

9. The process according to claim 8, wherein the hydrochlorination is carried out in the presence of the catalyst for hydrochlorinating the monochlorohydrin(s) and/or ester(s) thereof and/or multihydroxylated-aliphatic hydrocarbon compound(s) and/or ester(s) thereof.

10. The process according to claim 8, wherein the hydrochlorination is carried out using hydrogen chloride gas as the hydrochlorination agent; and wherein the hydrochlorination is carried out using a source of a superatmospheric partial pressure of hydrogen chloride as the hydrochlorination agent.

11. The process according to claim 8, wherein all of the steps of the process are carried out simultaneously with each other and the process is carried out continuously.

12. The process according to claim 8, wherein the distillation residue of step (b) is recycled to the hydrochlorination step.

13. The process according to claim 8, wherein the percent recovery of dichlorohydrin(s) produced during hydrochlorination is at least 90 percent.

14. The process according to claim 1, wherein the rate of byproduct formation in the process is less than 2 percent of the amount of dichlorohydrins produced in the process.

15. The process according to claim 1, wherein the liquid-vapor contacting device is a packed distillation column.

16. The process according to claim 15, wherein the distillation column contains structured packing.

* * * * *